(12) United States Patent
Reich et al.

(10) Patent No.: US 8,755,044 B2
(45) Date of Patent: Jun. 17, 2014

(54) LARGE PARTICLE DETECTION FOR MULTI-SPOT SURFACE SCANNING INSPECTION SYSTEMS

(75) Inventors: Juergen Reich, Campbell, CA (US); Charles Amsden, Mountain View, CA (US); Jiayao Zhang, Sunnyvale, CA (US); Christian Wolters, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 124 days.

(21) Appl. No.: 13/565,702

(22) Filed: Aug. 2, 2012

(65) Prior Publication Data

US 2013/0050689 A1 Feb. 28, 2013

Related U.S. Application Data

(60) Provisional application No. 61/523,481, filed on Aug. 15, 2011, provisional application No. 61/548,815, filed on Oct. 19, 2011.

(51) Int. Cl.
*G01N 21/956* (2006.01)

(52) U.S. Cl.
USPC ......... 356/237.4; 356/218; 356/337; 250/205

(58) Field of Classification Search
USPC ........... 356/237.1–237.5, 213, 218, 335–343; 250/205
See application file for complete search history.

(56) References Cited

U.S. PATENT DOCUMENTS

| | | | |
|---|---|---|---|
| 5,178,836 A * | 1/1993 | Kitamori et al. | 422/73 |
| 7,271,886 B2 * | 9/2007 | Witney et al. | 356/213 |
| 7,436,508 B2 | 10/2008 | Wolters et al. | |
| 7,671,982 B2 | 3/2010 | Wolters et al. | |
| 7,787,114 B2 | 8/2010 | Wolters et al. | |
| 2004/0262521 A1 * | 12/2004 | Devitt et al. | 250/341.1 |
| 2007/0132987 A1 * | 6/2007 | Haller et al. | 356/237.2 |
| 2009/0200279 A1 * | 8/2009 | Li | 219/121.66 |
| 2009/0225399 A1 | 9/2009 | Zhao et al. | |

(Continued)

FOREIGN PATENT DOCUMENTS

| | | |
|---|---|---|
| JP | 2007-279026 A | 10/2007 |
| JP | 2011-009554 A | 1/2011 |

OTHER PUBLICATIONS

International Search Report and Written Opinion mailed on Jan. 31, 2013, for PCT Application No. PCT/US2012/049541 filed on Aug. 3, 2012, by KLA-Tencor Corporation, 10 pages.

*Primary Examiner* — Hoa Pham
(74) *Attorney, Agent, or Firm* — Spano Law Group; Joseph S. Spano

(57) ABSTRACT

The illumination power density of a multi-spot inspection system is adjusted in response to detecting a large particle in the inspection path of an array of primary illumination spots. At least one low power, secondary illumination spot is located in the inspection path of an array of relatively high power primary illumination spots. Light scattered from the secondary illumination spot is collected and imaged onto one or more detectors without overheating the particle and damaging the wafer. Various embodiments and methods are presented to distinguish light scattered from secondary illumination spots. In response to determining the presence of a large particle in the inspection path of a primary illumination spot, a command is transmitted to an illumination power density attenuator to reduce the illumination power density of the primary illumination spot to a safe level before the primary illumination spot reaches the large particle.

20 Claims, 13 Drawing Sheets

(56) References Cited

U.S. PATENT DOCUMENTS

2010/0090108 A1* 4/2010 Hoeche .................. 250/307
2010/0195097 A1 8/2010 Wenz
2012/0229802 A1* 9/2012 Wolters et al. ............. 356/237.5

* cited by examiner

LARGE PARTICLE DETECTION FOR MULTI-SPOT SURFACE SCANNING INSPECTION SYSTEMS

CROSS REFERENCE TO RELATED APPLICATION

The present application for patent claims priority under 35 U.S.C. §119 from U.S. provisional patent application Ser. No. 61/548,815, entitled "Methods of Reducing Thermal Damage and Extending the Detection Range for a Multi-Spot Inspection System," filed Oct. 19, 2011, and from U.S. provisional patent application Ser. No. 61/523,481, entitled "Method of Simultaneously Sensing Wafer Position and Detecting Large Particles," filed Aug. 15, 2011. The subject matter of each of the aforementioned U.S. provisional patent applications is incorporated herein by reference.

TECHNICAL FIELD

The described embodiments relate to systems for surface inspection, and more particularly to simultaneous, multiple spot inspection modalities.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

One such inspection system is a multi-spot wafer inspection system that illuminates and inspects a number of different areas of a wafer surface, simultaneously. Improvements to multi-spot inspection systems are desired to detect large particles in the inspection path of multiple illumination spots on a wafer surface and prevent thermal damage to the wafer surface by reducing illumination power density at large particle locations.

SUMMARY

The illumination power density of a multi-spot inspection system is adjusted in response to detecting a large particle in the inspection path of an array of primary illumination spots. Multi-spot inspection system 100 determines the presence of a large particle in the inspection path of a plurality of incident spots of an incident spot array based on light scattered from at least one low power, secondary illumination spot located in the inspection path of an array of relatively high power primary illumination spots. Light scattered from the secondary illumination spot is collected and imaged onto one or more detectors without overheating the particle and damaging the wafer. Multi-spot inspection system 100 generates a control signal to reduce the incident illumination power density before a relatively high power portion of any of the primary illumination spots reach the large particle. An illumination power density attenuator reduces the illumination power density of at least one of the primary illumination spots to a safe level before the primary illumination spot reaches the large particle.

Secondary illumination spots may be located in the inspection path of a number of primary illumination spots in a number of different arrangements. In some embodiments, an individual secondary illumination spot is sized to span the areas to be illuminated by the primary illumination spots. In some other embodiments, a number of secondary illumination spots are spatially separated. Each of the secondary illumination spots are located ahead of a corresponding primary illumination spot and are individually sized to span the area to be illuminated by each corresponding primary illumination spot. In some embodiments, a secondary illumination spot 121 is located relatively far ahead along the inspection path of the primary illumination spots. In some other embodiments, a secondary illumination spot 121 is located relatively close to a corresponding primary illumination spot.

In some embodiments, a single detector of multi-spot inspection system 100 receives an amount of light scattered from the primary illumination spots and at least two secondary illumination spots consecutively located in the inspection path of at least one primary illumination spot. In one example, an illumination power density controller receives a signal from a detector indicating the amount of scattered light received from the consecutively located secondary illumination spots. The illumination power density controller determines if the detected light exceeds a predetermined threshold value at two different times spaced apart by a predetermined period of time, the conclusion is made that a large particle has been encountered by the pair of consecutively located secondary illumination beams. In response, illumination power density controller transmits a command signal to an illumination power density attenuator to reduce the illumination power density of at least one of the primary illumination spots.

In some embodiments, at least two secondary illumination spots are consecutively located and oriented askew from one another. In one example, an illumination power density controller receives a signal from a detector indicating the amount of scattered light received from the consecutively located secondary illumination spots. The illumination power density controller determines two consecutive times when the signal exceeds a predetermined threshold value and the time difference between these two instances. Because the secondary illumination spots are arranged askew, the distance between the secondary illumination spots varies as a function of location on the wafer surface. Moreover, because the geometry of the secondary illumination spots and the motion trajectory of the wafer surface are known, the illumination power density controller determines the location of a large particle on the wafer surface based on the time difference between the two instances when the signal exceeds a predetermined threshold value.

In some other embodiments, an amount of light that is specularly reflected from a secondary illumination spot is detected by a detector and used to determine the fly height of a wafer surface. Thus, in addition to using light scattered from a secondary illumination spot to regulate the illumination power density of primary illumination spots, light that is specularly reflected is used to detect changes in wafer height.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
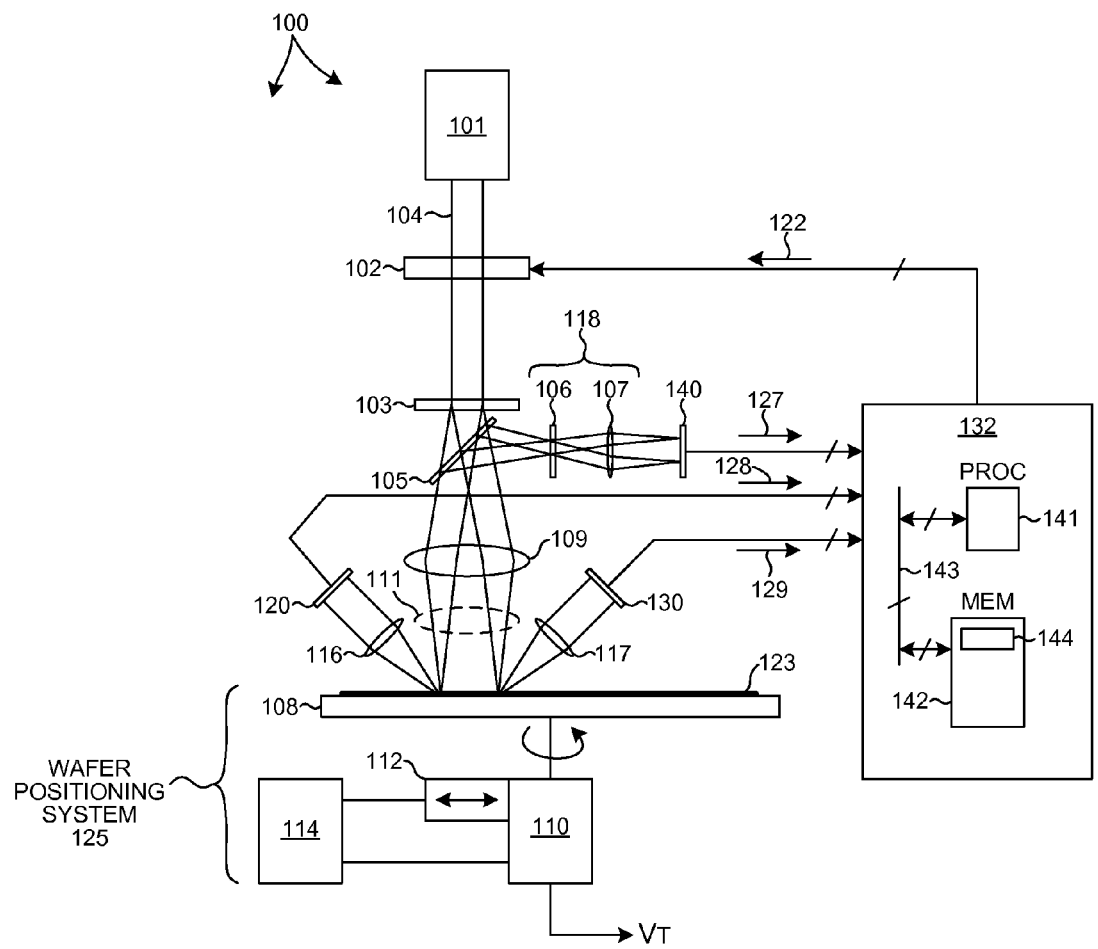
FIG. 1 is a simplified diagram illustrative of one embodiment of a multi-spot inspection system 100 that may be used to perform the inspection methods described herein.

FIG. 1 is a simplified schematic view of one embodiment of a multi-spot inspection system 100 that may be used to perform the inspection methods described herein. For simplification, some optical components of the system have been omitted. By way of example, folding mirrors, polarizers, beam forming optics, additional light sources, additional collectors, and detectors may also be included. All such variations are within the scope of the invention described herein. The inspection system described herein may be used for inspecting patterned, as well as unpatterned wafers.

As illustrated in FIG. 1, a wafer 123 is illuminated by a normal incidence beam 104 generated by one or more illumination sources 101. Alternatively, the illumination subsystem may be configured to direct the beam of light to the specimen at an oblique angle of incidence. In some embodiments, system 100 may be configured to direct multiple beams of light to the specimen such as an oblique incidence beam of light and a normal incidence beam of light. The multiple beams of light may be directed to the specimen substantially simultaneously or sequentially.

Illumination source 101 may include, by way of example, a laser, a diode laser, a helium neon laser, an argon laser, a solid state laser, a diode pumped solid state (DPSS) laser, a xenon arc lamp, a gas discharging lamp, and LED array, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

Figure 2:
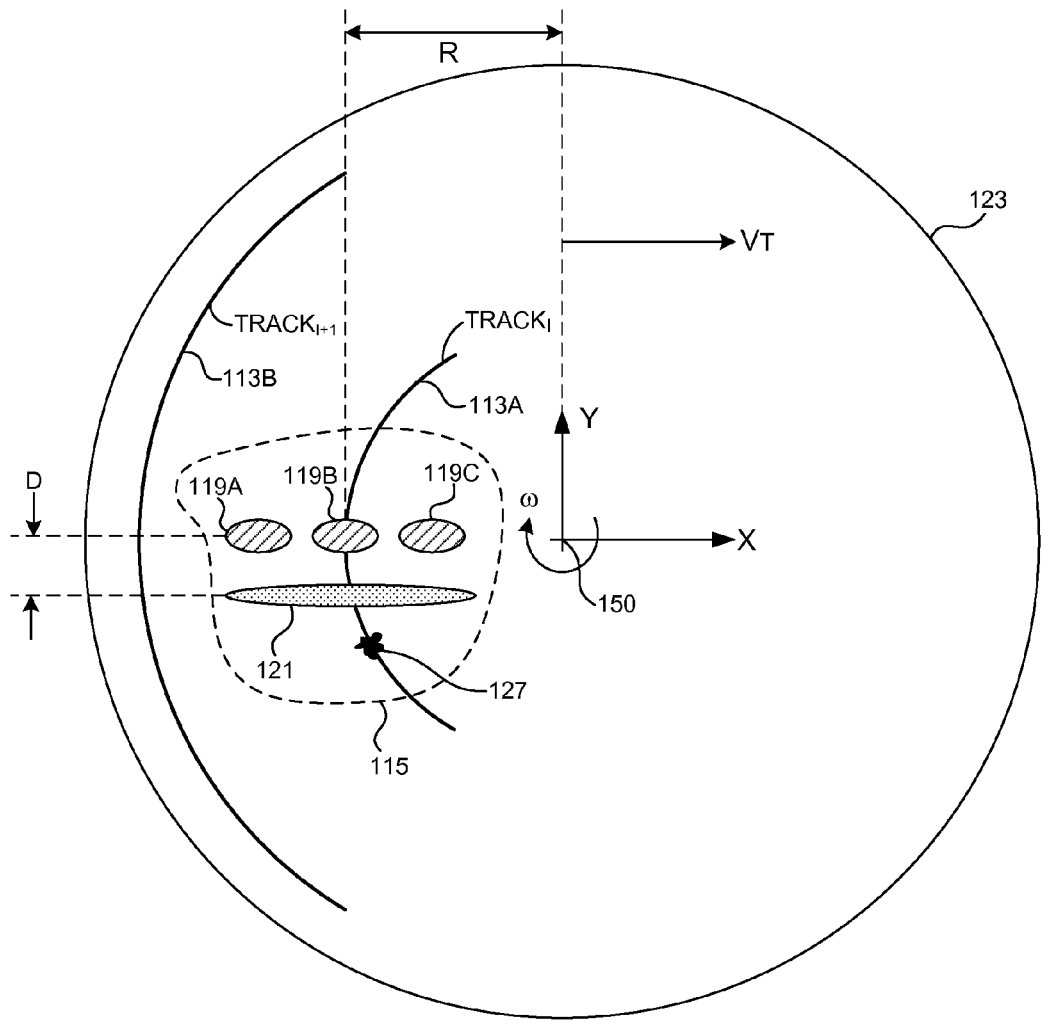
FIG. 2 is a simplified diagram illustrative of a wafer 123 illuminated by an incident spot array 115 that includes a number of primary illumination spots and at least one secondary illumination spot 121 in one embodiment.

System 100 includes a spot array generator 103 that generates a desired beamlet array 111 from the output of illumination source 101. This "generated beamlet array" is directed to the wafer surface. To eliminate confusion, the light that reaches the surface of the wafer is referred to herein as the "incident beamlet array" or the "incident spot array" (e.g., incident spot array 115 illustrated in FIG. 2). The "incident spot array" may differ from the "generated beamlet array" in one or more ways, including polarization, intensity, size and shape of the spot, etc. In one embodiment, spot array generator 103 includes a diffractive optical element to generate the desired number of spots, size of each spot, and spacing between spots. The size, number, and spacing between spots may be determined by a user or may be automatically generated by system 100. A beam splitter 105 directs the beamlet array to an objective lens 109. Objective lens 109 focuses the beamlet array 111 onto a wafer 123 to form incident spot array 115. As illustrated in FIG. 2, incident spot array 115 is located a distance, R, from the geometric center of wafer 123. In this manner, incident spot array 115 is defined (i.e., shaped and sized) by the projection of light emitted from spot array generator 103 onto the surface of wafer 123.

System 100 includes collection optics 116, 117, and 118 to collect the light scattered and/or reflected by wafer 123 during the scan and focus that light onto detector arrays 120, 130, and 140, respectively. The outputs of detectors 120, 130, and 140 are supplied to a computer 132 for processing the signals and determining the presence of anomalies and their characteristics. An image of the scanned area can be obtained by re-arranging the outputs from the plurality of channels (e.g., from each of detector arrays 120, 130, and 140), which have been stored in a memory 142 of a computer 132.

Any of collection optics 116-118 may be a lens, a compound lens, or any appropriate lens known in the art. Alternatively, any of collection optics 116-118 may be a reflective or partially reflective optical component, such as a mirror. In addition, although particular collection angles are illustrated in FIG. 1, it is to be understood that the collection optics may be arranged at any appropriate collection angle. The collection angle may vary depending upon, for example, the angle of incidence and/or topographical characteristics of the specimen.

Each of detectors 120, 130, and 140 generally function to convert the scattered light into an electrical signal, and therefore, may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes and photomultiplier tubes (PMTs) may be used, depending on the amount of light available for inspection and the type of inspection being performed. In at least one embodiment of the invention, a photomultiplier tube is used for detecting light scattered from a specimen. The term "single detector" is used herein to describe a detector having only one sensing area, or possibly several sensing areas (e.g., a detector array or multi-anode PMT). Regardless of number, the sensing areas of a single detector are embodied within a single enclosure.

System 100 also includes various electronic components (not shown) needed for processing the scattered signals detected by any of detectors 120, 130, and 140. For example, system 100 may include amplifier circuitry to receive output signals from any of detectors 120, 130, and 140 and to amplify those output signals by a predetermined amount and an analog-to-digital converter (ADC) to convert the amplified signals into a digital format suitable for use within processor 141. In one embodiment, the processor may be coupled directly to ADC 22 by a transmission medium. Alternatively, the processor may receive signals from other electronic components coupled to the ADC. In this manner, the processor may be indirectly coupled to the ADC by a transmission medium and any intervening electronic components.

In general, processor 141 is configured to detect features, defects, or light scattering properties of the wafer using electrical signals obtained from each detector. The signals produced by the detector are representative of the light detected by a single detector (e.g., detector 120, detector 130, or detector 140). The processor may include any appropriate processor known in the art. In addition, the processor may be configured to use any appropriate defect detection algorithm or method known in the art. For example, the processor may use a die-to-database comparison or a thresholding algorithm to detect defects on the specimen.

In addition, multi-spot inspection system 100 may include peripheral devices useful to accept inputs from an operator (e.g., keyboard, mouse, touchscreen, etc.) and display outputs to the operator (e.g., display monitor). Input commands from an operator may be used by processor 141 to adjust threshold values used to control illumination power. The resulting power levels may be graphically presented to an operator on a display monitor.

System 100 can use various imaging modes, such as bright field, dark field, and confocal. For example, in one embodiment, detector array 140 generates a bright field image. As illustrated in FIG. 1, some amount of light scattered from the surface of wafer 123 at a narrow angle is collected by objective lens 109. This light passes back through objective lens 109 and impinges on beam splitter 105. Beam splitter 105 transmits a portion of the light to collection optics 118, which in turn focuses the light onto detector array 140. In this manner a bright field image is generated by detector array 140. Collection optics 118 include imaging lens 107 that images the reflected light collected by objective lens 109 onto detector array 140. An aperture or Fourier filter 106, which can rotate in synchronism with the wafer, is placed at the back focal plane of objective lens 109. Various imaging modes such as bright field, dark field, and phase contrast can be implemented by using different apertures or Fourier filters. U.S. Pat. Nos. 7,295,303 and 7,130,039, which are incorporated by reference herein, describe these imaging modes in further detail. In another example, detector arrays 120 and 130 generate dark field images by imaging scattered light collected at larger field angles. In another example, a pinhole array that matches the layout of the illumination spot array can be placed in front of each detector array 120, 130, and 140 to generate a confocal image. U.S. Pat. No. 6,208,411, which is incorporated by reference herein, describes these imaging modes in further detail. In addition, various aspects of surface inspection system 100 are described in U.S. Pat. No. 6,271,916 and U.S. Pat. No. 6,201,601, both of which are incorporated herein by reference.

In the embodiment illustrated in FIG. 1, wafer positioning system 125 moves wafer 123 under a stationary beamlet array 111. Wafer positioning system 125 includes a wafer chuck 108, motion controller 114, a rotation stage 110 and a translation stage 112. Wafer 123 is supported on wafer chuck 108. As illustrated in FIG. 2, wafer 123 is located with its geometric center 150 approximately aligned the axis of rotation of rotation stage 110. In this manner, rotation stage 110 spins wafer 123 about its geometric center at a specified angular velocity, $\omega$, within an acceptable tolerance. In addition, translation stage 112 translates the wafer 123 in a direction approximately perpendicular to the axis of rotation of rotation stage 110 at a specified velocity, $V_T$. Motion controller 114 coordinates the spinning of wafer 123 by rotation stage 110 and the translation of wafer 123 by translation stage 112 to achieve the desired scanning motion of wafer 123 within multi-spot inspection system 100.

In an exemplary operational scenario, inspection begins with incident spot array 115 located at the geometric center 150 of wafer 123 and then wafer 123 is rotated and translated until incident spot array 115 reaches the outer perimeter of wafer 123 (i.e., when R equals the radius of wafer 123). Due to the coordinated motion of rotation stage 110 and translation stage 112, the locus of points illuminated by incident spot array 115 traces a spiral path on the surface of wafer 123. The spiral path on the surface of wafer 123 is referred to as an inspection track 113 (not shown in its entirety). Portions 113a and 113b of an exemplary inspection track 113 are illustrated in FIG. 2 as $TRACK_i$ and $TRACK_{i+1}$, respectively. The distance between adjacent portions of an inspection track (e.g., distance between $TRACK_{i+1}$ and $TRACK_i$) is referred to as the scan pitch of the multi-spot inspection system 100. Incident spot array 115 may be configured with considerable spacing between beamlets such that inspection results are interleaved among successive portions of a track 113 and cross-talk at the detectors is minimized. U.S. Pat. Publication No. 2009/0225399, which is incorporated by reference herein, describes multi-spot scanning techniques in further detail.

In some embodiments, system 100 may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

In high-power laser-based inspection systems, the power density of the incident laser beam typically ranges between about 1 kW/cm$^2$ to about 1000 kW/cm$^2$. Unfortunately, particle damage often occurs during surface inspection scans with high power density laser beams, due to the rapid power transfer from the laser beam to a particle (or a portion of a particle) on the specimen. Particles not capable of dissipating large amounts of power tend to warm up quickly, and often explode due to insufficient power dissipation. For example, organic materials (such as photoresist particles) tend to dissipate significantly less power than inorganic materials (such as metallic particles), and therefore, tend to experience more damage. Unfortunately, exploded particles lead to debris, which can spread a large area of contamination over the specimen.

On the contrary, the inventive concepts described herein are based on the observation that larger particles (e.g., particles greater than five microns in diameter) are more likely to be damaged by the incident laser beam than smaller particles. For example, larger particles have more surface area, and as such, tend to absorb significantly more power than smaller particles having less surface area. Larger particles also tend to scatter significantly more light than smaller particles, due to larger surface area and/or increased surface irregularities. For example, the amount of light scattered from a particle of radius, R, is relatively proportional to the particle radius raised to the sixth power.

The inventive concepts described herein exploit the highly scattering properties of large particles to reduce thermal damage during a multi-spot surface inspection scan. In one novel aspect, multi-spot inspection system 100 implements illumination power density control functionality that determines the presence of a large particle in the inspection path of a plurality of primary illumination spots of an incident spot array and generates a control signal to reduce the incident illumination power density before a relatively high power portion of any of the primary illumination spots reach the large particle. In this manner, thermal damage may be avoided.

Multi-spot inspection system 100 includes a processor 141 and an amount of computer readable memory 142. Processor 141 and memory 142 may communicate over bus 143. Memory 142 includes an amount of memory 144 that stores a program code that, when executed by processor 141, causes processor 141 to determine the presence of a large particle in the inspection path of a plurality of primary illumination spots of an incident spot array and generate a control signal that causes an illumination power density attenuator to reduce the illumination power density delivered to the wafer 123 before a relatively high power portion of any of the primary illumination spots reach the large particle. In the depicted embodiments, the illumination power density attenuator is an illumination power attenuator 102 that reduces the illumination power delivered to wafer 123. In some other embodiments, the illumination power density attenuator is a beam shaping element (e.g., spot array generator 103) that resizes at least one of the primary illumination spots to reduce the illumination power density delivered to wafer 123. In some other embodiments, a combination of illumination power reduction and beam sizing is employed to reduce the illumination power density delivered to wafer 123.

In the depicted embodiments, computer 132 includes processor 141 and memory 142 and implements illumination power density control functionality of a multi-spot inspection system in accordance with the methods described herein. Hence, in some embodiments, computer 132 is an illumination power density controller as described herein. However, in other embodiments, illumination power density control functionality may be implemented by any other general purpose computer or dedicated hardware of multi-spot inspection system 100 configured to operate in an analogous manner.

Figure 14:
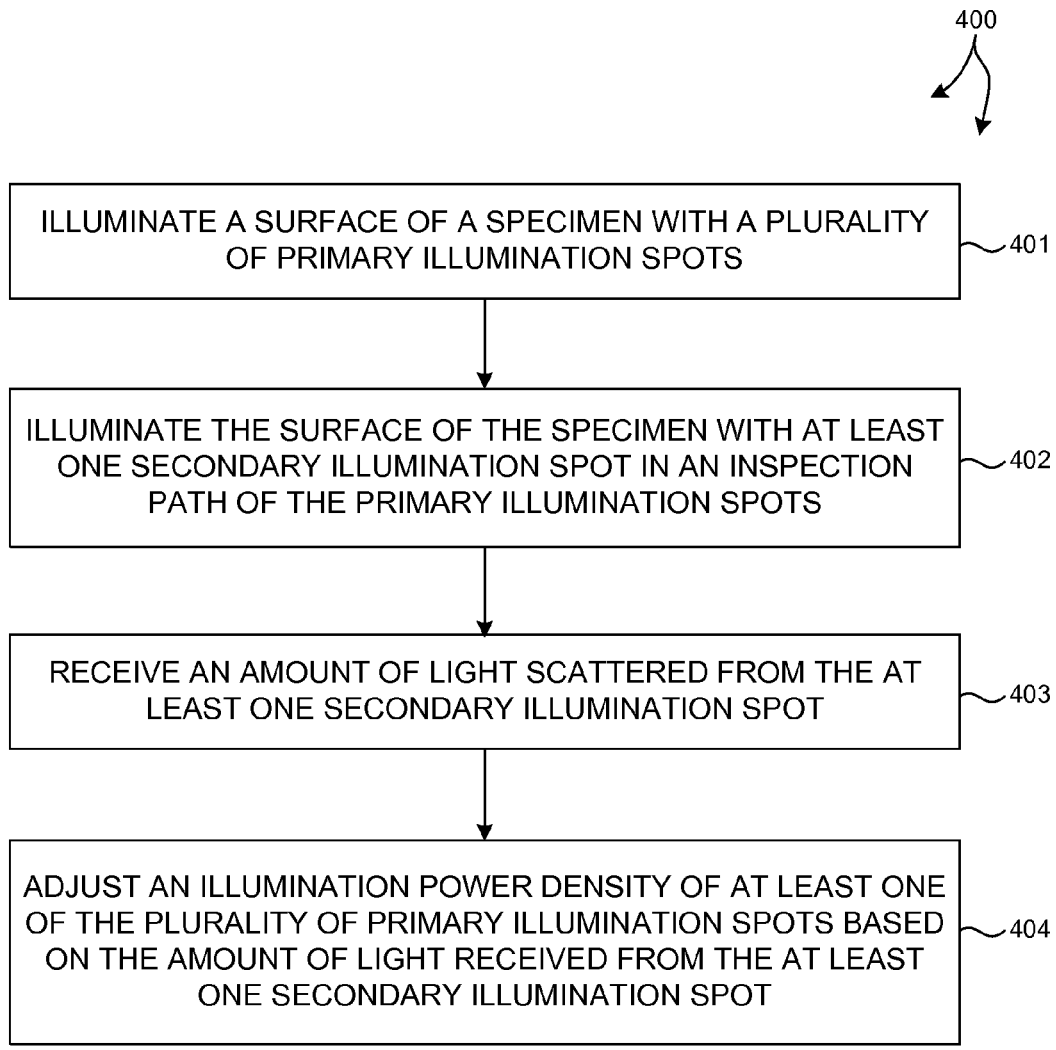
FIG. 14 is a flowchart illustrative of a method 400 of adjusting the illumination power density of a multi-spot inspection system 100.

FIG. 1 illustrates a multi-spot inspection system 100 that implements the inspection methods described herein. In one example, multi-spot inspection system 100 implements a method 400 illustrated in FIG. 14. In block 401, multi-spot inspection system 100 illuminates a surface of a specimen with a plurality of primary illumination spots. In block 402, multi-spot inspection system 100 illuminates the surface of the specimen with at least one secondary illumination spot in an inspection path of the primary illumination spots.

Referring to FIG. 2 by way of example, incident spot array 115 includes primary illumination spots 119A-C and a secondary illumination spot 121. Although, three primary illumination spots and one secondary illumination spot are depicted, it is understood that any number of primary and secondary illumination spots may be employed. Primary illumination spots 119A-C are relatively high power illumination spots useful for imaging of the surface of wafer 102. Typically, primary illumination spots 119A-C are spaced apart from one another to minimize cross-talk at the detector surface or surfaces that image the light collected from these spots. By way of non-limiting example, primary illumination spots may be sized between one and five hundred microns in either of the planar dimensions (e.g., x and y dimensions) and may be spaced apart by a distance that is at least the size of the smaller dimension defining the primary illumination spot. Secondary illumination spot 121 is a relatively low power illumination spot useful for detecting large particles present on the surface of the wafer without inducing damage. Secondary illumination spot 121 is located in the inspection path of the primary illumination spots along the motion trajectory of the incident spot array 115. In this manner, the relatively low power secondary illumination spot 121 encounters a large particle before any of the relatively high power primary illumination spots. Secondary illumination spot 121 has an illumination power density that is less than a primary illumination spot. In one non-limiting example, the illumination power density is less than 50% of the illumination power density of the primary illumination spots 119. In another non-limiting example, the illumination power density of the secondary illumination spot 121 is less than 25% of the illumination power density of the primary illumination spots 119.

Figure 4:
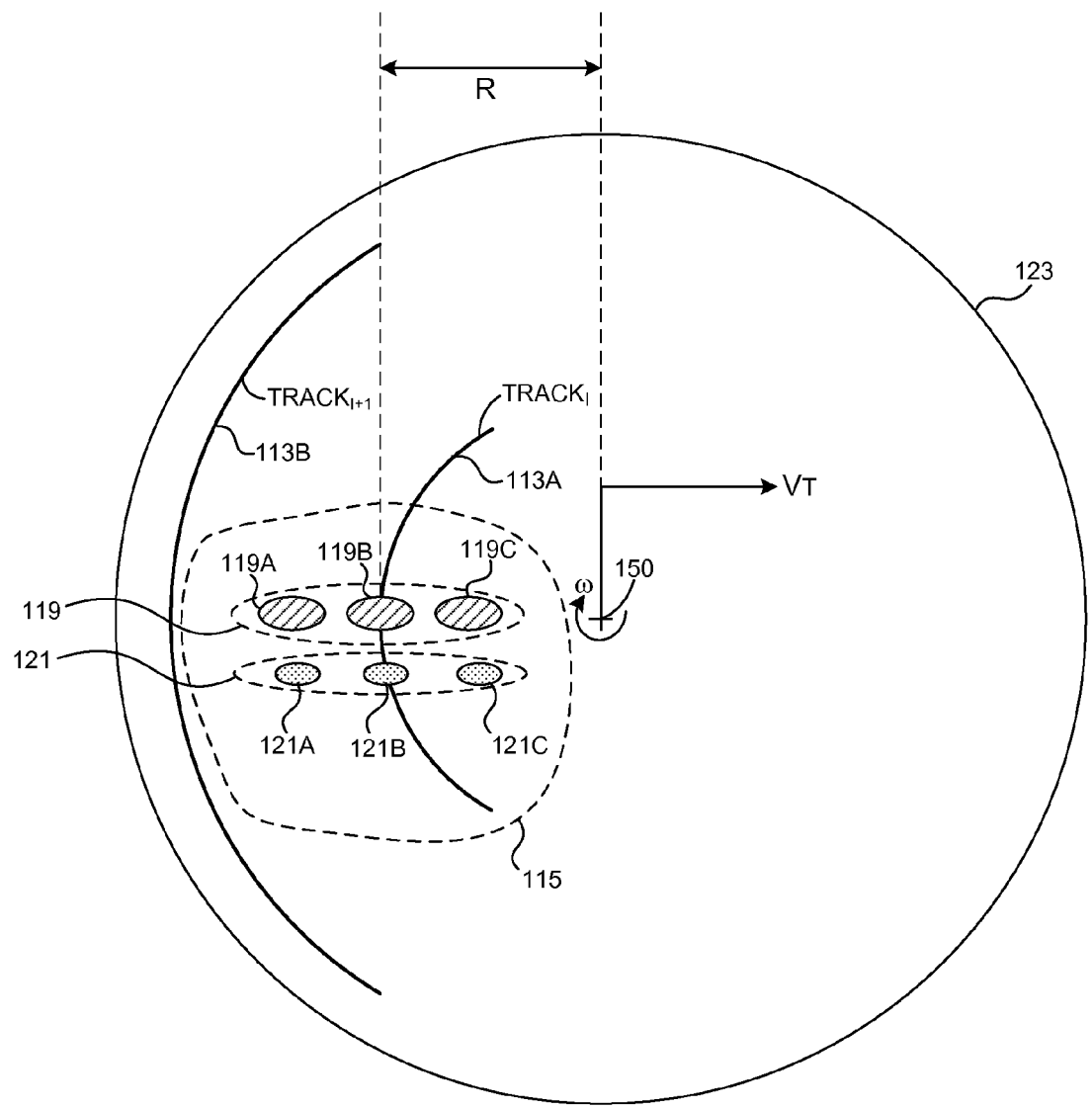
FIG. 4 is a simplified diagram illustrative of a wafer 123 illuminated by an incident spot array 115 that includes a number of primary illumination spots and at least one secondary illumination spot 121 in another embodiment.

In some examples, secondary illumination spot 121 is sized to span the areas to be illuminated by primary illumination spots 119. However, other shapes, locations, and numbers of secondary illumination spots may be contemplated. For example, as illustrated in FIG. 4, secondary illumination spots 121A-C may be spatially separated, each located ahead of a corresponding primary illumination spot 119 and individually sized to span the area to be illuminated by each corresponding primary illumination spot 119A-C. This may be preferred over a single, large secondary illumination spot to avoid excessive waste of illumination energy when primary illumination spots 119 are widely separated. In another example, illustrated in FIG. 5, secondary illumination spot 121 is located relatively far ahead along the inspection path of the primary illumination spots 119. This may be preferred to further separate the secondary and primary illumination spots and avoid cross-talk on the detector or detectors. However, by locating the secondary illumination spot 121 a larger distance from the primary illumination spots 119, the knowledge of location of a large particle illuminated by the secondary illumination spot 121 becomes less precise. As a result, primary illumination power must be reduced over a larger area to minimize the risk of large particle "blow-up," thereby reducing the amount of wafer area subject to inspection at maximum sensitivity.

In block 403, a detector of multi-spot inspection system 100 receives an amount of light scattered from the at least one secondary illumination spot. In the embodiment depicted in FIG. 1, collection optics 117 are arranged to collect light scattered from secondary illumination spot 121 and direct the light to detector 130. Detector 130 receives the scattered light and generates a signal 129 indicating the amount of scattered light incident upon the detector and transmits the signal to illumination power density controller 132.

Figure 15:
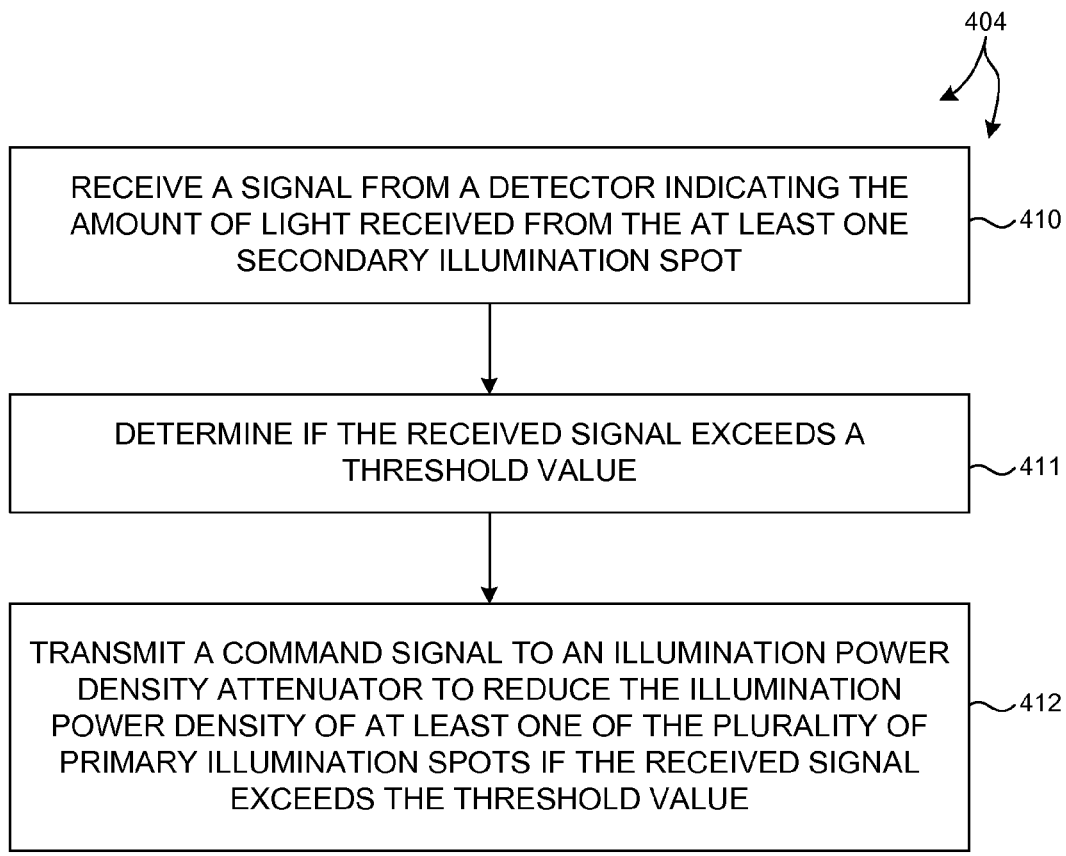
FIG. 15 is a flowchart illustrative of one exemplary method 404 of adjusting the illumination power density of at least one of a plurality of primary illumination spots based on light scattered from at least one secondary illumination spot.

In block 404, multi-spot inspection system 100 adjusts the illumination power density of at least one of the primary illumination spots 119 based on the amount of light scattered from the secondary illumination spot. In one example of block 404, illustrated in FIG. 15, illumination power density controller 132 receives the signal 129 from detector 130 indicating the amount of scattered light received from the secondary illumination spot 121 (block 410). In block 411, illumination power density controller 132 compares this signal with a predetermined threshold value to determine if the amount of scattered light exceeds the threshold value.

Figure 3:
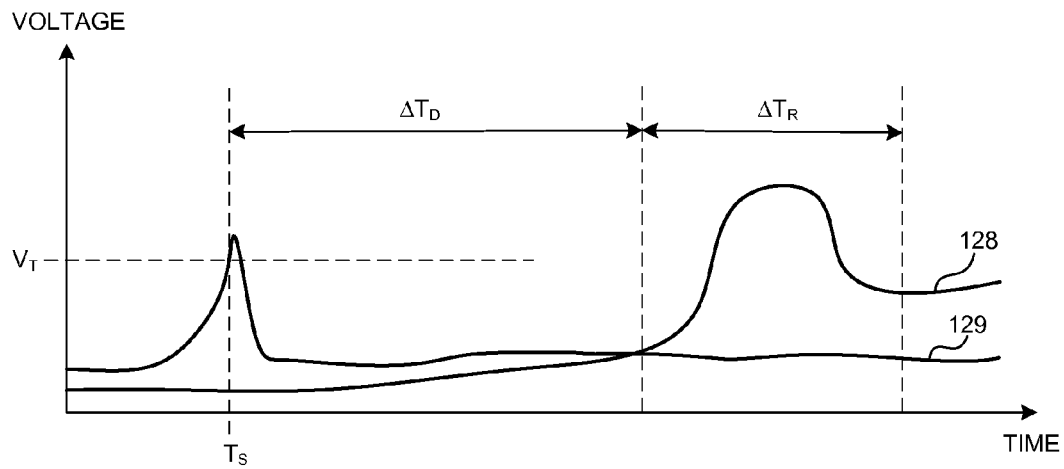
FIG. 3 is a plot 310 illustrative of signals 128 and 129 indicative of light scattered from primary illumination spots and at least one secondary illumination spot, respectively.

Referring to FIG. 3, a time plot of signal 129 is depicted for illustrative purposes. At a time, $T_s$, the voltage level of signal 129 exceeds a predetermined threshold value, $V_T$. At this time, illumination power density controller 132 determines that the amount of scattered light from secondary illumination spot 121 exceeds the threshold value. Threshold value, $V_T$, may be selected automatically or manually. Typically, threshold value, $V_T$, is selected such that values of signal 129 below the threshold indicate a particle size that poses minimal risk of thermal damage when interacting with any of the primary illumination spots 119. In block 412, illumination power density controller 132 transmits a command signal 122 to illumination power density attenuator 102 to reduce the illumination power density of at least one of the primary illumination spots 119 when the amount of scattered light from secondary illumination spot 121 exceeds the threshold value. In some examples, illumination power density controller 132 may transmit command signal 122 immediately. However, in other examples, illumination power density controller 132 may delay transmitting the command signal 122 until a period of time, $\Delta T_D$, has past. In one example, illumination power density controller 132 may determine a delay period, $\Delta T_D$, based on the known velocity of the wafer surface under inspection (e.g., $V_s = \omega*R + V_T$) and the known distance between the secondary illumination spot 121 and the primary illumination spots 119 (e.g., $\Delta T_D = D/V_s$). In some examples, illumination power density controller 132 may command illumination power density attenuator 102 to continue to reduce power until signal 129 falls below the threshold value. However, in some other examples, illumination power density controller 132 may command illumination power density attenuator 102 to reduce illumination power density for a predetermined period of time, $\Delta T_D$. This period of time may be selected to ensure that sufficient time has passed before illumination power density is returned to normal inspection levels. As illustrated in FIG. 3, signal 128, indicative of an amount of light scattered from the primary illumination spots 119, is muted during the period, $\Delta T_R$, when the illumination power density is reduced.

To adjust the incident illumination power density, illumination power density attenuator 102 adjusts the power level of the incident light supplied to the wafer in response to the command signal 122 generated by the illumination power density controller 132. For example, illumination power density attenuator 102 may be arranged between illumination source 101 and spot array generator 103 to dynamically adjust the illumination power during a surface inspection scan. In general, illumination power density attenuator 102 may be implemented with a selectively transmissive optical component, which may be adapted to transmit a portion of the incident light based on a polarization of the incident light. In some embodiments, illumination power density attenuator 102 may include a wave plate (such as a quarter wave plate) and a polarizing beam splitter. In this configuration, the wave plate may be used to change the polarization of the incoming light, while the beam splitter functions to transmit one or more select polarizations (e.g., linearly polarized light) and reflect all others (e.g., randomly, circularly or elliptically polarized light). By reflecting portions of the light, the wave plate and beam splitter function to reduce the intensity or power level of the light transmitted there through. However, wave plates and similar optical components (e.g., neutral density filters) cannot be turned on and off like a switch, and instead, must be moved in and out of the beam path to provide two distinct power levels. In some cases, such movement may not be fast enough to provide dynamic power alteration during a surface inspection scan.

In a preferred embodiment of illumination power density attenuator 102, extremely fast laser power attenuation is provided using an electro-optical material to switch between an "on" condition and an "off" condition. When "on," the electro-optical material changes the polarization of the incoming light into a predetermined polarization orientation. This so-called "re-polarized light" may then be supplied to a polarizing beam splitter, which may transmit only a portion of the re-polarized light, depending on the particular polarization output from the electro-optical switch. Remaining portions of the re-polarized light may be reflected and discarded (e.g., absorbed by a beam dump material). In some cases, the electro-optical material may switch between "on" and "off" conditions within a time span of a few nanoseconds to a few microseconds. In this manner, fast laser power attenuation can be provided by using an electro-optical switch, rather than moving a selectively transmissive optical element in and out of the beam path.

In a specific embodiment, illumination power density attenuator 102 may be implemented with a high-speed electrically-controlled optical shutter, known as a Pockel Cell. Initially, a Pockel Cell may be set in the "on" condition to allow the light generated by illumination source 101 to pass freely through illumination power attenuator 102. However, when the presence of a large particle is detected, the Pockel Cell may be switched to the "off" condition to change the polarization of the generated light to a different polarization, which can be at least partially filtered out by a polarizing beam splitter. To switch between the "on" and "off" conditions, an electrical voltage provided by a variable power supply may be supplied to the Pockel Cell to change the polarization of the light passed through the electro-optical material (typically, an electro-optical crystal). The voltage supplied to the Pockel Cell may be determined by control signal 122 communicated from computer 132 to the variable power supply of illumination power attenuator 102.

In one example, the voltage supplied to the Pockel Cell (i.e., causing the cell to switch to the "on" condition) may alter the characteristics of the electro-optical crystal so that it changes linearly polarized light into circularly polarized light, a phenomenon frequently referred to as a "quarter wave phase shift." If the circularly polarized light is supplied to a beam splitter, which is primarily configured for reflecting circularly polarized light, the intensity or power level of the light output from illumination power density attenuator 102 can be reduced by setting the Pockel Cell in the "on" condition. On the other hand, the intensity or power level of the light output from illumination power density attenuator 102 can be maintained (or increased) by setting the Pockel Cell in the "off" condition.

However, the intensity of the light output from illumination power density attenuator 102 is dependent on the polarizing beam splitter, as well as the phase shift produced by the Pockel cell 200. For example, beam splitters typically discriminate between two orthogonal polarizations such as, e.g., the so-called "S" and "P" polarizations. However, other polarizations of light (such as C-polarized light) may be partially transmitted, and therefore, partially redirected (e.g. into the beam dump) by the beam splitter. If a voltage is applied such that the Pockel cell creates a ¼ wave phase shift, incoming linearly polarized light (typical laser output) will become circularly polarized and half of that light will pass through the beam splitter, while the other half is redirected. For a ½ wave shift, no light will pass through the beam splitter except for some leakage due to imperfection of the optical components. In other words, virtually all of the incoming light will be redirected when the Pockel Cell is configured to produce a ½ wave shift (assuming that in the power off state all light passes through the beam splitter).

In some cases, a constant power laser beam generated by illumination source 101 can be divided into two distinct power levels (e.g., a "safe" power level and a "full" power level) by dynamically switching an electro-optical shutter (such as a Pockel Cell) between "on" and "off" conditions. The safe power level may be substantially less than the full power level to prevent thermal damage when scanning over large particles. For example, the safe power level may be some percentage (ranging, e.g., between about 1% and about 50%) of the full power level. In one embodiment, the safe power level may be about 10% of the full power level. Other possibilities exist and may generally depend on the incident laser power, as well as the size and material composition of the particles being scanned.

In other cases, an electro-optical shutter (such as a Pockel Cell) may be configured for generating more than two distinct power levels. For example, a Pockel Cell can be driven to produce substantially any phase shift, and thus, may be combined with a polarizing beam splitter to create substantially any output power level. In other words, illumination power attenuator 102 could be used to create substantially any number of distinct power levels. In some cases, circuitry and/or software may be included to provide a continuous power level adjustment (e.g., in the form of a closed feedback loop).

In some other embodiments, a fast micro mirror, an acousto-optical deflector (AOD), or a fast mechanical shutter may be used to dynamically alter a power level of the incident light supplied to a wafer. As such, the present invention may encompass any appropriate means for dynamically altering the power level of an illumination source provided that such means provides a relatively fast response (e.g., on the order of a few nanoseconds to a few microseconds) and at least two distinct power levels (e.g., "safe" and "full" power levels). In general, the response time should be faster than the typical time it takes to damage a particle. Other factors that may influence the choice of a fast laser power attenuator include, but are not limited to, optical transmission, cost, reliability, and life-time.

In some embodiments, the illumination power density is adjusted by adjusting the incident spot size alone or in combination with the illumination power. In one example, the command signal 122 generated by the illumination power density controller 132 is transmitted to a beam shaping element (e.g., spot array generator 103). The beam shaping element increases the incident spot size in response to the command signal 122. In this manner illumination power density at the wafer level is reduced during a surface inspection scan.

As discussed herein, reflected and scattered light collected from the wafer surface may be associated with either a primary or secondary illumination spot based on spatial location on a detector. However, distinguishing between reflected and scattered light associated with a primary illumination spot or a secondary illumination spot may also be based on the wavelength of the collected light when different wavelength light is used to generate the primary and secondary illumination spots. In this manner, detector signals originating from primary illumination spots can be distinguished from signals originating from secondary illumination spots even when the primary and secondary illumination spots are located close together on the wafer surface (e.g., less than 500 microns apart).

As illustrated in FIG. 1, a single primary illumination source 101 supplies the illumination energy for both the primary and secondary illumination spots. In some embodiments, illumination source 101 may be a broadband source. The broadband light may be separated into different wavelength bands supplied to different spot array generators 103 to generate primary and secondary illumination spots of different wavelength. Similarly, light collected from the wafer surface may be separated into different wavelength bands and directed to different detectors (e.g., detectors 120 and 130). In this manner, detector signals originating from primary illumination spots are distinguished from signals originating from secondary illumination spots by wavelength rather than spatial location on the detector. By separating the collected light by wavelength, rather than spatial location, the primary and secondary illumination spots may be located close together on the wafer surface (e.g., less than 500 microns apart), thus improving the precision of large particle detection.

Figure 6:
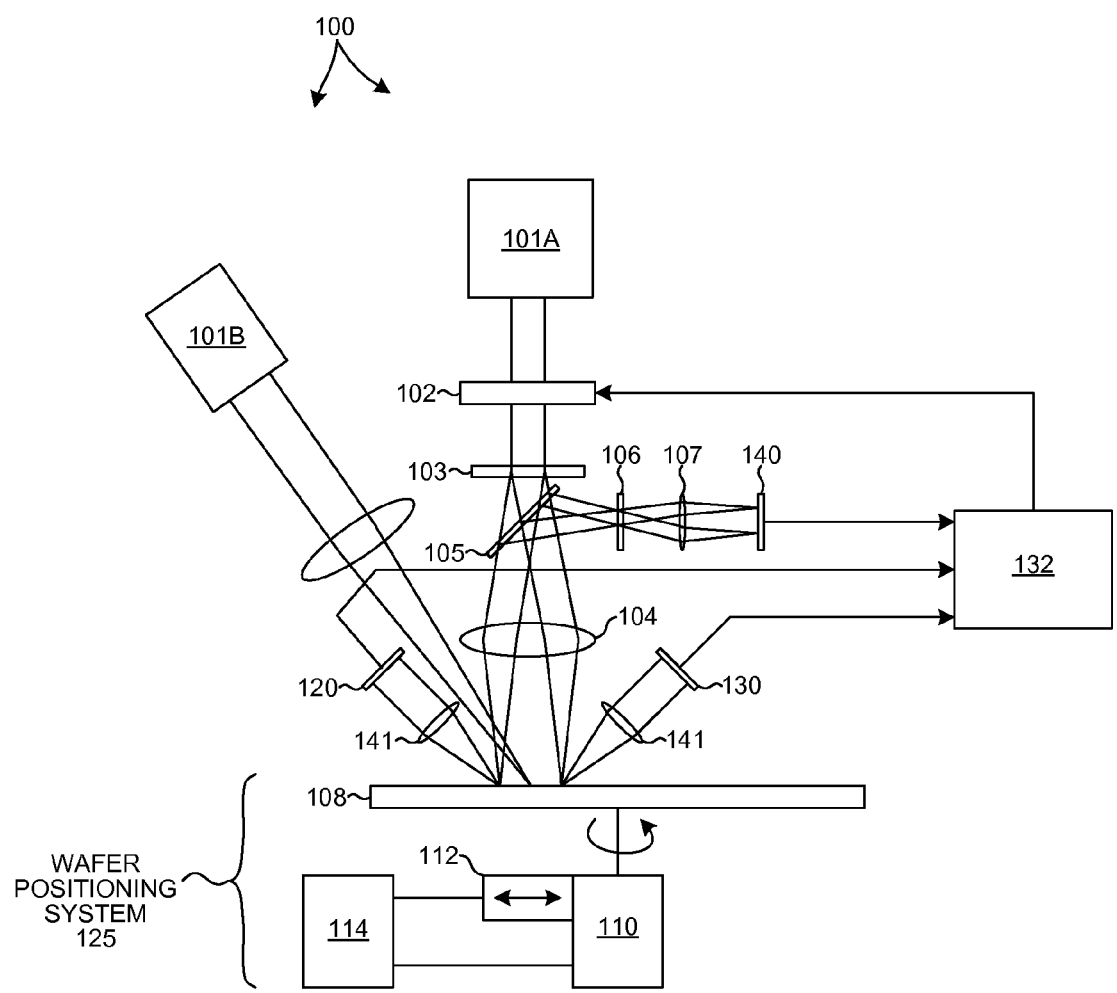
FIG. 6 is a simplified diagram illustrative of another embodiment of a multi-spot inspection system 100 that includes multiple illumination sources.

In another embodiment, depicted in FIG. 6, multi-spot inspection system 100 includes multiple illumination sources (e.g., illumination sources 101A-B). By way of non-limiting example, illumination source 101A may be a laser source tuned to supply light with a dominant wavelength of 266 nanometers used to generate the primary illumination spots 119. In addition, illumination source 101B may also be a laser source tuned to supply light with a dominant wavelength of 488 nanometers used to generate the secondary illumination spots. Other combinations of multiple illumination sources may also be contemplated.

Figure 5:
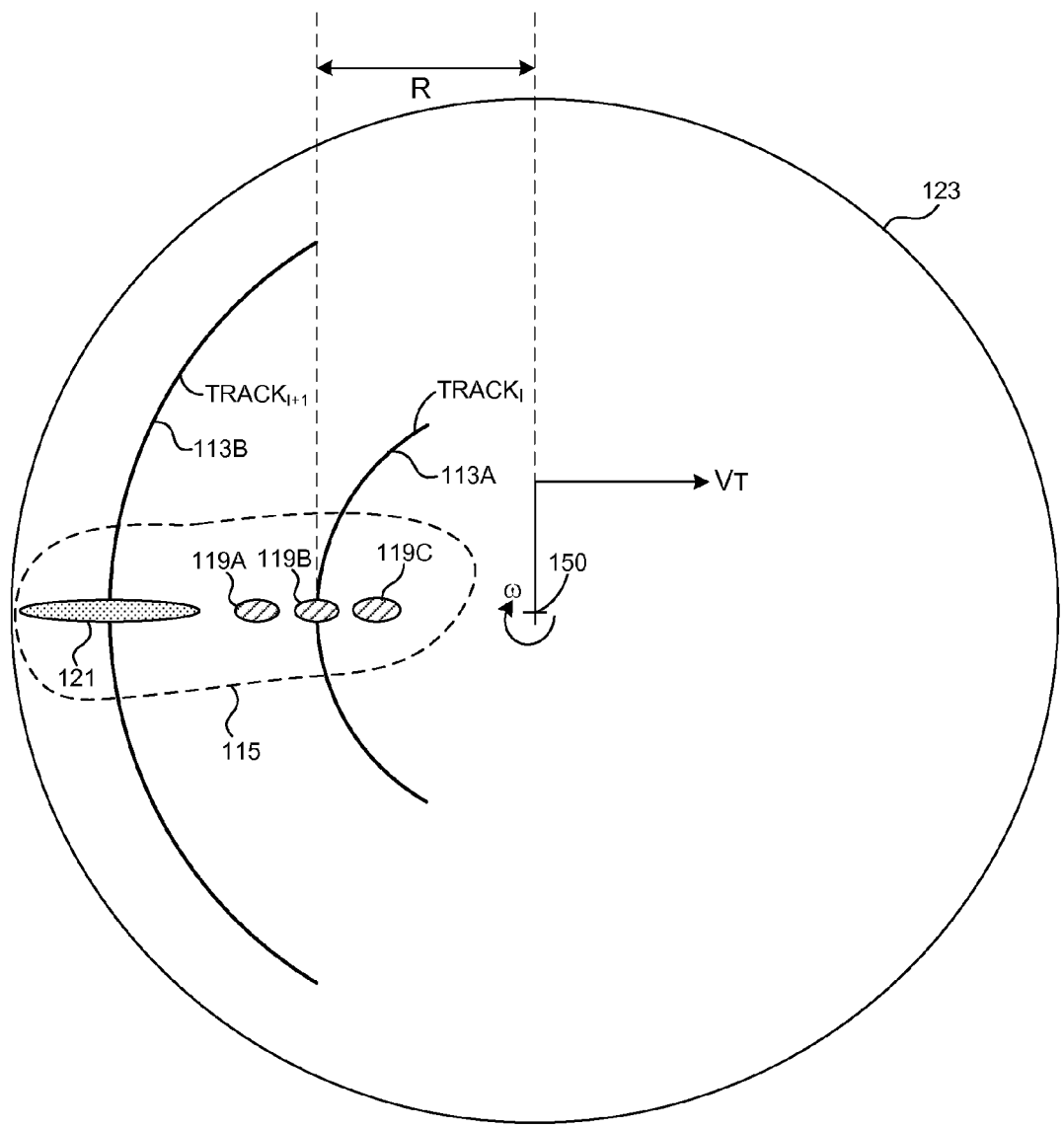
FIG. 5 is a simplified diagram illustrative of a wafer 123 illuminated by an incident spot array 115 that includes a number of primary illumination spots and at least one secondary illumination spot 121 in yet another embodiment.

As illustrated in FIG. 1 and FIG. 5, multiple detectors (e.g., detectors 120, 130, and 140) may be employed to image light collected from different spots on the wafer surface. This may be desirable to minimize the size of each detector when illumination spots are widely separated on the wafer surface. For example, different detectors may be employed to detect light scattered from primary illumination spots 119 and secondary illumination spot 121. As illustrated in FIGS. 1-4, a single detector (e.g., detector 140) may be employed to image light collected from primary illumination spots 119 and another detector (e.g., detector 130) may be employed to image light collected from secondary illumination spot 121. In another example, a single detector may be employed to detect light scattered from primary illumination spots 119 and a different detector may be employed to image each individual secondary illumination spot (e.g., secondary illumination spots 121A-C illustrated in FIG. 3). Similarly, other combinations of detectors may be contemplated.

It is necessary in some embodiments to distinguish between light scattered from primary illumination spots and light scattered from secondary illumination spots to detect large particles in time to reduce illumination power density of the primary illumination spots. As discussed herein, this may be accomplished by using different wavelength light sources or by having relatively large spatial separation between primary and secondary illumination spots (often requiring multiple detectors and sets of collection optics) to capture scattered light. However, in some other embodiments, multi-spot illumination system 100 is able to detect the presence of a large particle using at least two secondary illumination spots of the same wavelength and closely located to a primary illumination spot. In a preferred embodiment, only a single illumination source and a single detector are employed. In some embodiments, illumination power controller density 132 is able to determine the presence of a large particle in the inspection path of a primary illumination spot 119 by determining a characteristic of the time response of a single detector. The characteristic indicates an interaction between the large particle and a pair of secondary illumination spots arranged consecutively in the inspection path of at least one primary illumination spot.

Figure 8:
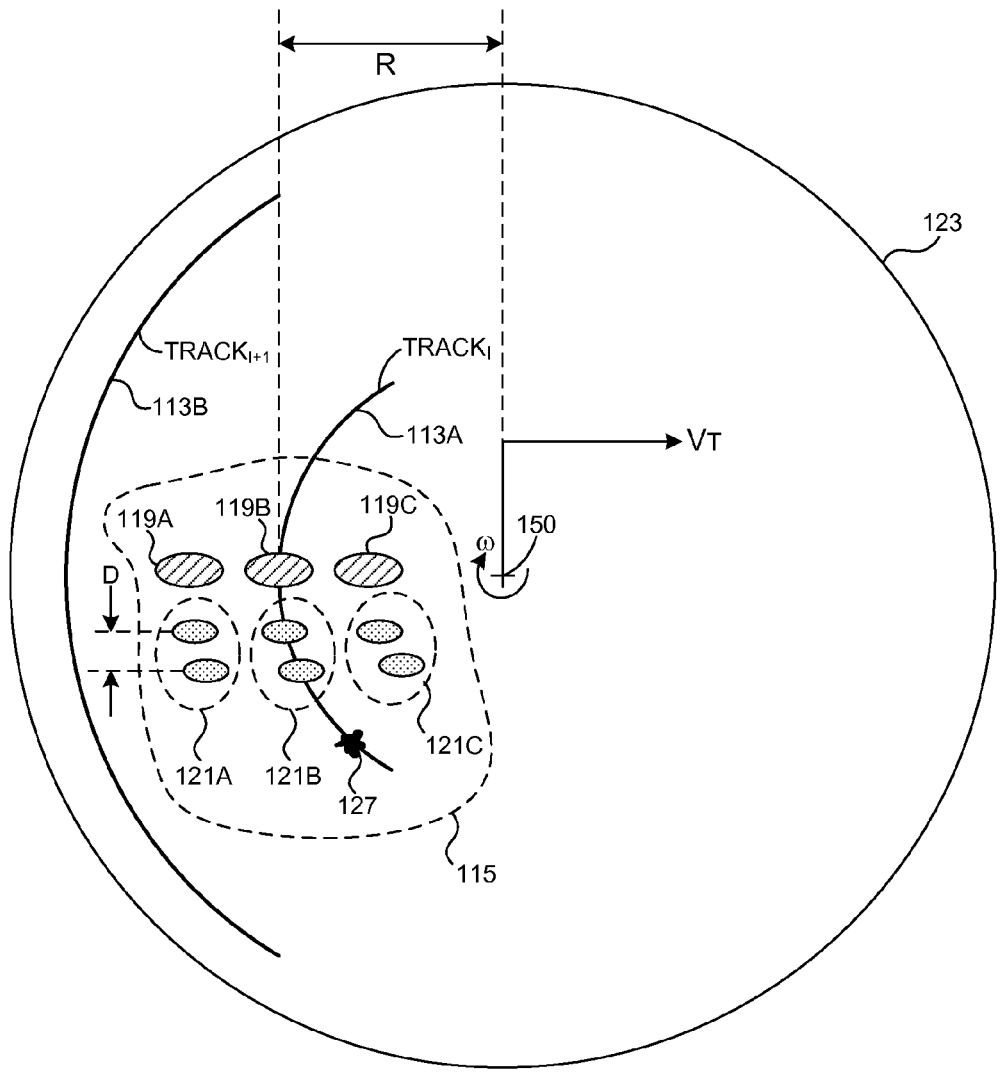
FIG. 8 is a simplified diagram illustrative of a wafer 123 illuminated by an incident spot array 115 that includes a number of primary illumination spots and at least one secondary illumination spot 121 in yet another embodiment.

Referring to FIG. 8, by way of example, incident spot array 115 includes primary illumination spots 119A-C and pairs of secondary illumination spots 121A-C. The pairs of secondary illumination spots 121A-C are located close to the primary illumination spots along the motion trajectory of the incident spot array 115. In some embodiments, a secondary illumination spot may be within one hundred microns of a corresponding primary illumination spot.

Figure 7:
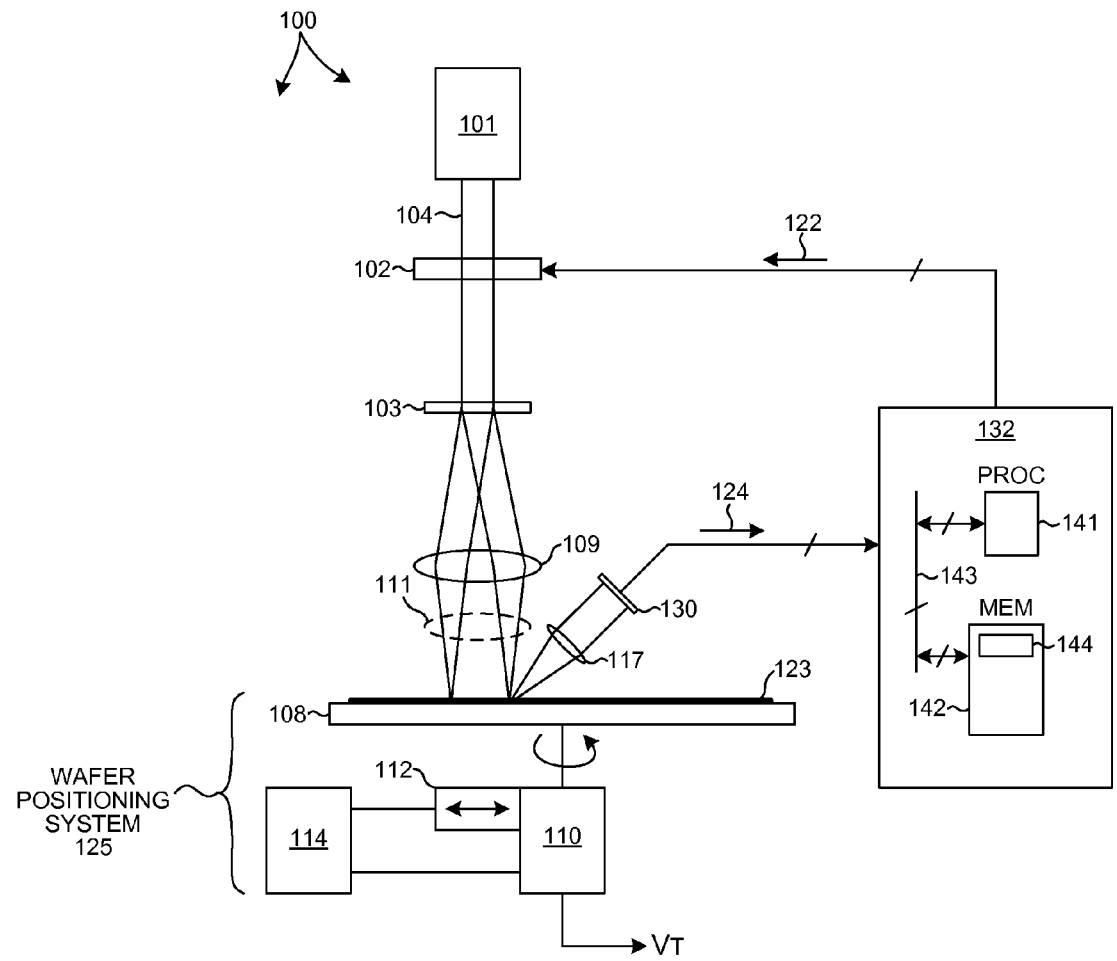
FIG. 7 is a simplified diagram illustrative of another embodiment of a multi-spot inspection system 100 that includes a single detector to detect light scattered from both primary illumination spots and at least one secondary illumination spot.

In some embodiments a single detector of multi-spot inspection system 100 receives an amount of light scattered from the primary illumination spots and the secondary illumination spots. For example, in the embodiment depicted in FIG. 7, collection optics 117 are arranged to collect light scattered from secondary illumination spot 121 and direct the light to detector 130. Detector 130 receives the scattered light and generates a signal 124 indicating the amount of scattered light incident upon the detector and transmits the signal to illumination power density controller 132.

Figure 16:
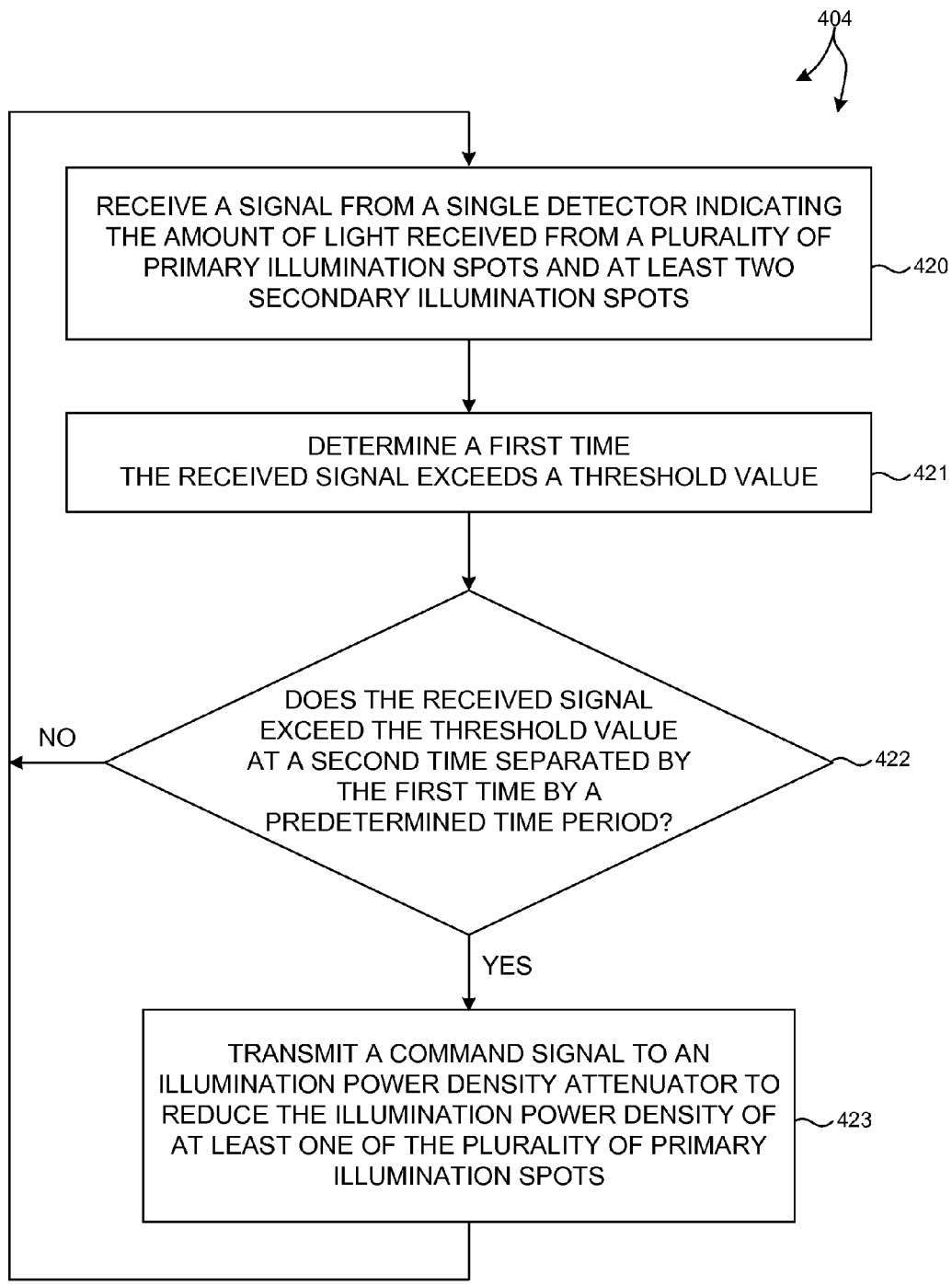
FIG. 16 is a flowchart illustrative of another exemplary method 404 of adjusting the illumination power density of at least one of a plurality of primary illumination spots based on light scattered from at least one secondary illumination spot.

Illumination power density controller 132 receives the signal 124 from detector 130 indicating the amount of scattered light received from the secondary illumination spot 121 (see block 410 illustrated in FIG. 16). In block 421, illumination power density controller 132 compares this signal with a predetermined threshold value to determine if the amount of scattered light exceeds the threshold value.

Figure 9:
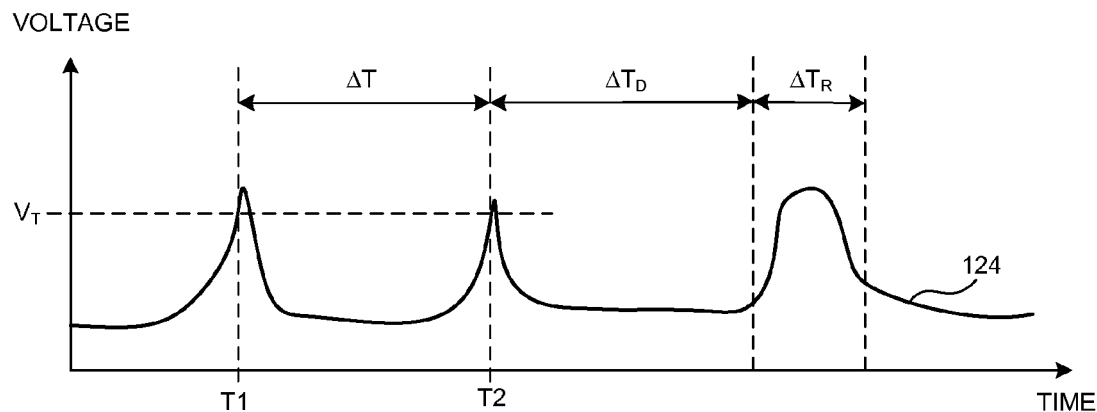
FIG. 9 is a plot illustrative of signal 124 indicative of light scattered from primary illumination spots and at least one secondary illumination spot.

Referring to FIG. 9, a time plot of signal 124 is depicted for illustrative purposes. At a time, $T_1$, the voltage level of signal 124 exceeds a predetermined threshold value, $V_T$. In block 422, the illumination power density controller 132 determines whether signal 124 exceeds the predetermined threshold value, $V_T$, at time $T_2$. Times, $T_1$ and $T_2$ are separated from each other by a predetermined period of time, $\Delta T$. In some embodiments, the predetermined period of time is selected automatically by multi-spot inspection system 100 by dividing a known distance, D, between each pair of secondary illumination spots by the known velocity of the wafer surface under inspection (e.g., $V_s=\omega*R+V_T$). When illumination power density controller 132 determines that signal 124 exceeds the threshold value at time $T_1$ and again at time $T_2$, the conclusion is made that a large particle has been encountered by the pair of secondary illumination beams rather than some other geometry encountered by a primary illumination beam. In response, illumination power density controller 132 transmits a command signal 122 to illumination power density attenuator 102 to reduce the illumination power density of at least one of the primary illumination spots 119 (see block 423).

In some examples, illumination power density controller 132 may transmit command signal 122 immediately. However, in other examples, illumination power density controller 132 may delay transmitting the command signal 122 until a period of time, $\Delta T_D$, has past. In one example, illumination power density controller 132 may determine a delay period, $\Delta T_D$, based on the known velocity of the wafer surface under inspection (e.g., $V_s=\omega*R+V_T$) and the known distance between the secondary illumination spot 121 and the primary illumination spots 119 (e.g., $\Delta T_D=D/V_s$). In some examples, illumination power density controller 132 may command illumination power density attenuator 102 to continue to reduce power density until signal 129 falls below the threshold value. However, in some other examples, illumination power density controller 132 may command illumination power density attenuator 102 to reduce illumination power density for a predetermined period of time, $\Delta T_D$. This period of time may be selected to ensure that sufficient time has passed before illumination power density is returned to normal inspection levels. As illustrated in FIG. 9, signal 124, indicative of an amount of light scattered from the wafer surface, is muted during the period, $\Delta T_R$, when the illumination power density is reduced.

In some embodiments, illumination power density controller 132 is able to resolve the location of a large particle with sufficient accuracy to determine which primary illumination spot of a plurality of primary illumination spots is likely to interact with the large particle.

Figure 10:
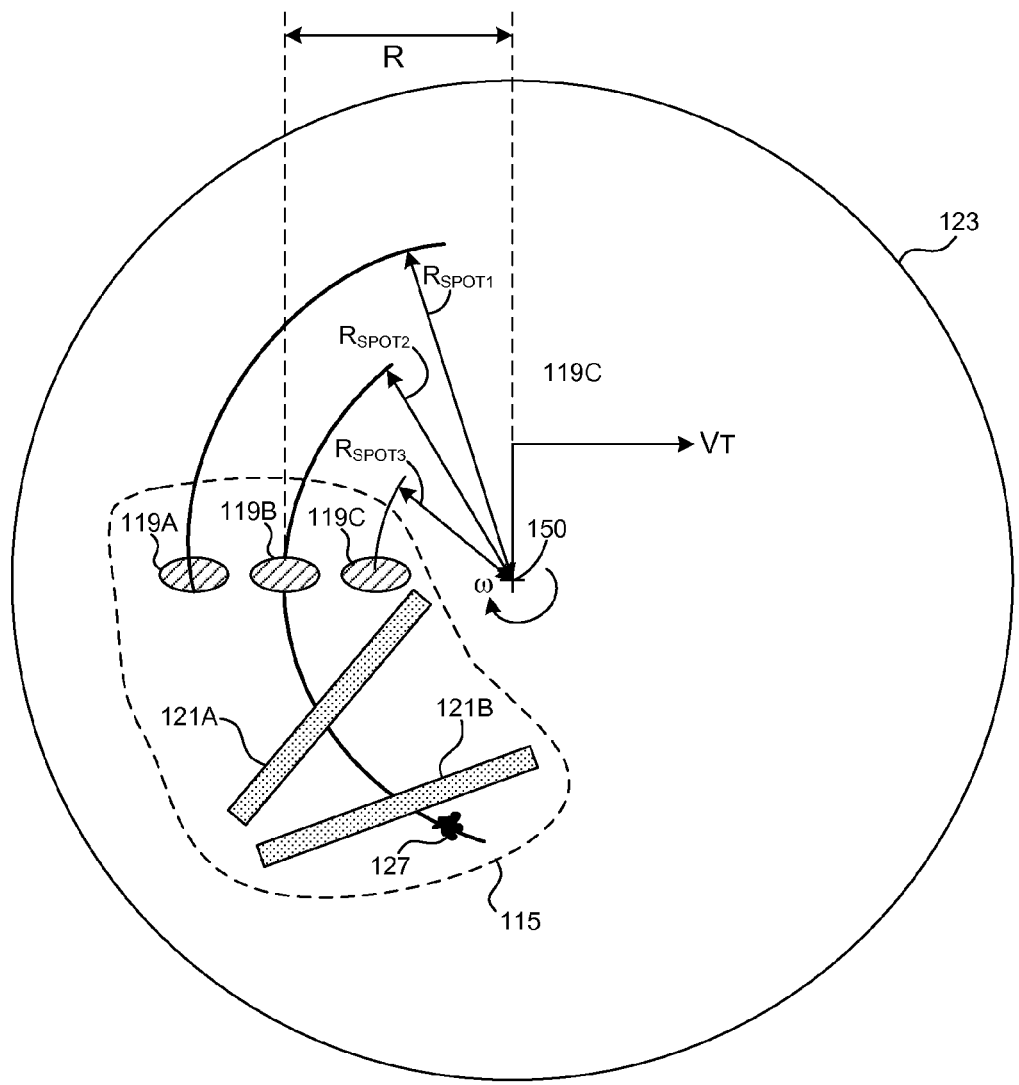
FIG. 10 is a simplified diagram illustrative of a wafer 123 illuminated by an incident spot array 115 that includes a number of primary illumination spots and at least two secondary illumination spots 121 in yet another embodiment.
Figure 11:
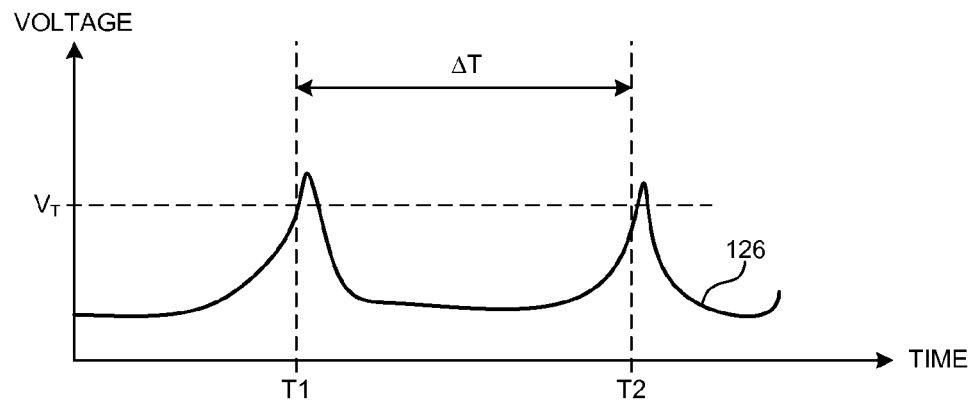
FIG. 11 is a plot illustrative of signal 126 indicative of light scattered from the at least two secondary illumination spots 121A and 121B.
Figure 12:
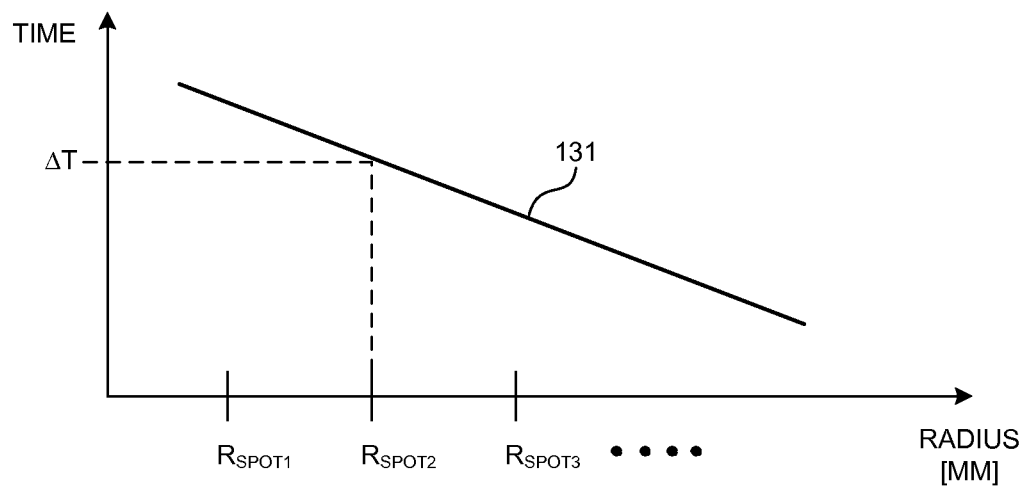
FIG. 12 is a plot 131 illustrative of the relationship between a characteristic of signal 126 and a location on wafer 123.
Figure 17:
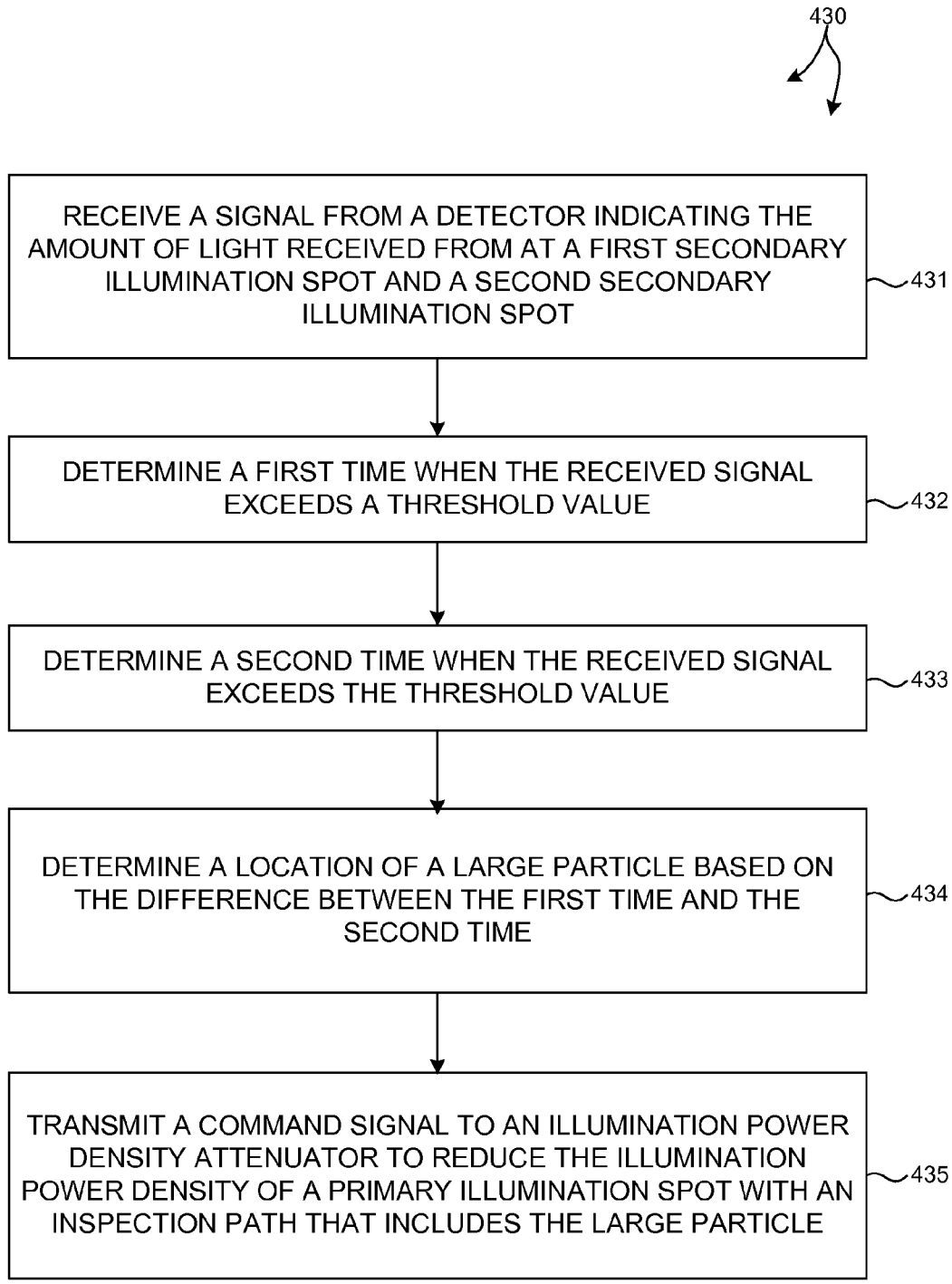
FIG. 17 is a flowchart illustrative of one exemplary method 430 of locating a large particle in the inspection path of at least one of a plurality of primary illumination spots based on light scattered from at least two secondary illumination spots.

FIG. 17 illustrates a flowchart of an exemplary method 430 useful for determining which primary illumination spot of a plurality of primary illumination spots is likely to interact with a large particle in accordance with FIGS. 10-12. In block 431, power illumination density controller 132 receives a signal 126 from detector 130 indicating an amount of light received from secondary illumination spots 121A and 121B. As illustrated in FIG. 10, multi-spot inspection system 100 employs at least two rectangular shaped secondary illumination spots 121A-B oriented askew from one another. Each of secondary illumination spots 121A and 121B spans the inspection path of the primary illumination spots 119. Secondary illumination spots 121A and 121B are arranged consecutively in the inspection path of the primary illumination spots 119. In block 432, illumination power density controller 132 determines a first time, $T_1$, when the received signal 126 exceeds a predetermined threshold value, $V_T$. In block 433, illumination power density controller 132 determines a second time, $T_2$, when the received signal 126 exceeds the predetermined threshold value, $V_T$. In block 434, illumination power density controller 132 determines the location of a large particle based on the time difference between $T_1$ and $T_2$.

Referring to FIG. 11, a time plot of signal 126 is depicted for illustrative purposes. At times, $T_1$ and $T_2$, the voltage level of signal 126 exceeds a predetermined threshold value, $V_T$. Because the secondary illumination spots are consecutively arranged, this indicates that a large particle 127 has interacted with both secondary illumination spots 121A and 121B. In addition, because the secondary illumination spots are arranged askew, the distance between the secondary illumination spots 121A and 121B varies across the inspection path of primary illumination spots 119 in a known manner. For example, as illustrated in FIG. 10, the distance between secondary illumination spots 121A and 121B varies linearly as a function of radius from the center of wafer 123. Thus, the distance between secondary illumination spots 121A and 121B in an inspection path of primary illumination spot 119C is greater than the distance in an inspection path of primary illumination spot 119A. Furthermore, the velocity of the wafer surface under inspection is known (e.g., $V_s=\omega*R+V_T$). Based on the known distance between secondary illumination spots 121A and 121B and the known velocity of the wafer under inspection, an expected time between interactions of a large particle with secondary illumination spots 121A and 121B can be determined. For example, FIG. 12 illustrates a plot 131 relating the expected time between interactions of a large particle with secondary illumination spots 121A and 121B and the distance, $R_{spot}$, between a particular primary illumination spot and the center of wafer 123. Illumination power density controller 132 can determine the time elapsed between a large particle interaction with secondary illumination spot 121B at time, $T_1$ and secondary illumination spot 121A at time, $T_2$. Based on this time difference, $\Delta T$, the location (e.g., $R_{spot2}$) of the large particle within the inspection path of primary illumination spot 119B can be determined.

By way of example, plot 131 can be calculated automatically by multi-spot inspection system 100 and stored in a look-up table in memory 142 such that illumination power controller 132 can look-up a spot location based on $\Delta T$. Alternatively, the relationship between elapsed time and spot location can be expressed in functional terms (e.g., $R_{spot}=f(\Delta T)$) and the spot location can be calculated by illumination power density controller 132 based on $\Delta T$.

At block 435, illumination power density controller 132 transmits a command signal 122 to a illumination power density attenuator 102 to reduce the illumination power density of a primary illumination spot with an inspection path that includes the large particle. By way of example, illumination power density attenuator 102 may be a number of illumination power density attenuators, each configured to regulate the illumination power density of an individual or subset of primary illumination spots. In this manner, the presence of a large particle in the inspection path of one of the primary illumination spots 119 does not require a power density reduction of all of the primary illumination spots. Instead the illumination power density of the primary illumination spot that will interact with the large particle is reduced.

In another aspect, an amount of light reflected from a secondary illumination spot is detected by a separate detector and used to determine wafer height. In many of the embodiments discussed, herein, light scattered from secondary illumination spots is detected and used to regulate the illumination power density of primary illumination spots. However, in addition, light that is specularly reflected from a secondary illumination spot can be detected by a separate detector and used to determine wafer height. In one example, this wafer height measurement can be used to drive an autofocus system of multi-spot inspection system 100.

Figure 13:
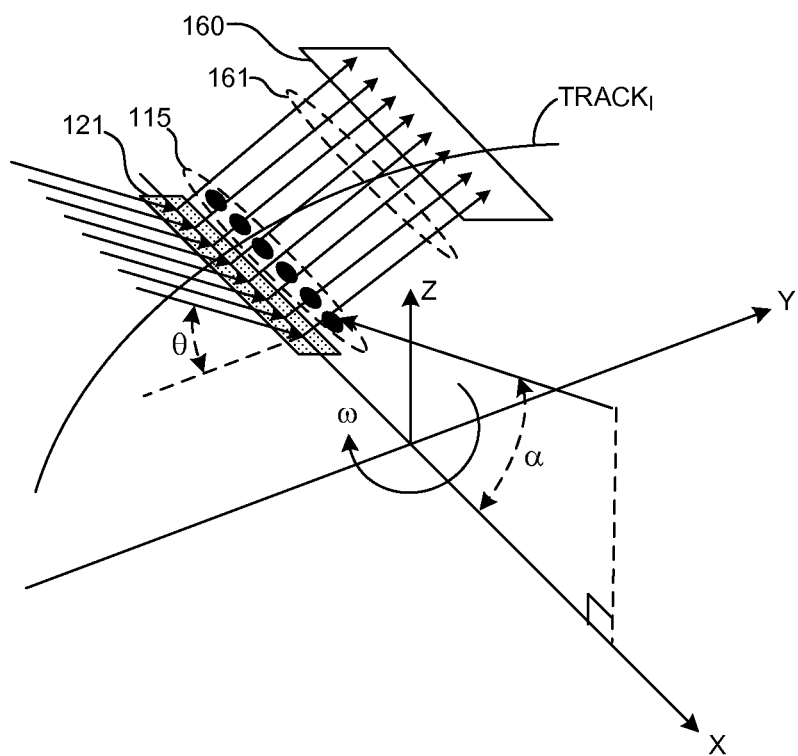
FIG. 13 is a simplified diagram illustrative of a wafer 123 illuminated by an incident spot array 115 that includes a number of primary illumination spots and at least one secondary illumination spot 121 in yet another embodiment.

In one embodiment illustrated in FIG. 13, a wafer (not shown) is positioned in the x-y plane and rotates about the z-axis. As depicted, secondary illumination spot 121 is rectangular in shape and oriented parallel to an array 115 of primary illumination spots. An amount of light 161 is specularly reflected from the surface of the wafer under illumination by secondary illumination spot 121. The specularly reflected light 161 is received by detector 160. Changes in wafer height (illustrated in FIG. 13 as the z-direction) at the secondary illumination spot 121 are determined based on changes in the location of incidence of light 161 on the surface of detector 160.

As depicted in FIG. 13, secondary illumination is directed to the wafer surface at an approximately constant, oblique angle, $\theta$, from the wafer surface and parallel to the y-z plane. This ensures that specularly reflected light at detector 160 is properly focused. In addition, primary illumination is directed to the wafer surface at primary illumination spots 119 at an oblique angle, $\alpha$, from the wafer surface and parallel to the x-z plane. By delivering primary and secondary light to the wafer surface in orthogonal planes, cross-talk at detector 160 is minimized. In this manner, primary illumination may be normal or oblique or both without impacting the wafer height measurement based on specularly reflected light from secondary illumination spot 121.

Various embodiments are described herein for an inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. In one example, detectors arrays 120, 130, and 140 can be replaced by fiber arrays. In one example, multi-spot inspection system 100 may include more than one light source (not shown). The light sources may be configured differently or the same. For example, the light sources may be configured to generate light having different characteristics that can be directed to a wafer at the same or different illumination areas at the same or different angles of incidence at the same or different times. The light sources may be configured according to any of the embodiments described herein. In addition one of the light sources may be configured according to any of the embodiments described herein, and another light source may be any other light source known in the art. In some embodiments, a multi-spot system may illuminate the wafer over more than one illumination area simultaneously. The multiple illumination areas may spatially overlap. The multiple illumination areas may be spatially distinct. In some embodiments, a multi-spot system may illuminate the wafer over more than one illumination area at different times. The different illumination areas may temporally overlap (i.e., simultaneously illuminated over some period of time). The different illumination areas may be temporally distinct. In general, the number of illumination areas may be arbitrary, and each illumination area may be of equal or different size, orientation, and angle of incidence. In yet another example, multi-spot inspection system 100 includes secondary illumination spots used to detect the presence of large particles ahead of the primary inspection spots. However, multi-spot inspection system 100 may include multiple levels of large particle detection spots (e.g., ternary spots, etc.) arranged to detect large particles with greater resolution in accordance with the methods described herein. In yet another example, multi-spot inspection system 100 may be a scanning spot system with one or more illumination areas that scan independently from any motion of wafer 123. In some embodiments an illumination area is made to scan in a repeated pattern along a scan line. The scan line may or may not align with the scan motion of wafer 123. Although as presented herein, wafer positioning system 125 generates motion of wafer 123 by coordinated rotational and translational movements, in yet another example, wafer positioning system 100 may generate motion of wafer 123 by coordinating two translational movements. For example motion wafer positioning system 125 may generate motion along two orthogonal, linear axes (e.g., X-Y motion). In such embodiments, scan pitch may be defined as a distance between adjacent translational scans along either motion axis. In such embodiments, a multi-spot inspection system includes an illumination source and a wafer positioning system. The illumination source supplies an amount of radiation to a surface of a wafer over an illumination area. The wafer positioning system moves the wafer in a scanning motion characterized by a scan pitch (e.g., scanning back and forth in one direction and stepping by an amount equal to the scan pitch in the orthogonal direction). The wafer positioning system includes a motion controller that adjusts the scan pitch independently from the illumination area.

Accordingly, various modifications, adaptations, and combinations of various features of the described embodiments can be practiced without departing from the scope of the invention as set forth in the claims.

What is claimed is:

1. A method comprising:
    illuminating a surface of a specimen with a plurality of primary illumination spots over a first area;
    illuminating the surface of the specimen with at least one secondary illumination spot over a second area in an inspection path of the plurality of primary illumination spots;
    receiving an amount of light scattered from the at least one secondary illumination spot; and
    adjusting an illumination power density of at least one of the primary illumination spots based on the amount of scattered light received.

2. The method of claim 1, further comprising:
    receiving an amount of light specularly reflected from the at least one secondary illumination spot on a surface of a detector; and
    determining a change in height of the surface of the specimen based on a change in location of incidence of the amount of specularly reflected light received on the surface of the detector.

3. The method of claim 1, wherein the adjusting of the illumination power density involves:
    receiving a signal from a detector indicating the amount of light received from the at least one secondary illumination spot;
    determining if the received signal exceeds a predetermined threshold value; and
    transmitting a command signal to an illumination power density attenuator that causes the illumination power density attenuator to reduce an illumination power density of at least one of the plurality of primary illumination spots if the received signal exceeds the threshold value.

4. The method of claim 1, wherein the adjusting of the illumination power density involves:

receiving a signal from a single detector indicating an amount of light received from the plurality of primary illumination spots and at least two secondary illumination spots;
determining a first time the received signal exceeds a predetermined threshold value;
determining if the received signal exceeds the predetermined threshold value at a second time that is a predetermined period of time after the first time; and
transmitting a command signal to an illumination power density attenuator that causes the illumination power density attenuator to reduce an illumination power density of at least one of the plurality of primary illumination spots if the received signal exceeds the threshold value at the second time.

5. The method of claim 1, wherein the illuminating of the surface of the specimen with the plurality of primary illumination spots over the first area involves a first amount of radiation characterized by a first wavelength, and wherein the illuminating of the surface of the specimen with the at least one secondary illumination spot over the second area involves a second amount of radiation characterized by a second wavelength.

6. The method of claim 1, further comprising:
moving the specimen in a scanning motion such that the specimen tracks a predetermined motion trajectory.

7. A multi-spot inspection system comprising:
a first detector operable to receive a first amount of light scattered from a plurality of primary illumination spots incident on a first portion of a surface of a wafer;
a second detector operable to receive a second amount of light scattered from at least one secondary illumination spot on a second portion of the surface of the wafer; and
an illumination power density controller operable to receive a signal indicating the second amount of scattered light and transmit a command signal to an illumination power density attenuator to reduce an illumination power density of the multi-spot inspection system based on the received signal.

8. The multi-spot inspection system of claim 7, further comprising:
a wafer positioning system operable to move the wafer in a scanning motion such that the primary illumination spots move across the surface of the wafer along an inspection path.

9. The multi-spot inspection system of claim 8, wherein the at least one secondary illumination spot is located ahead of the primary illumination spots in the inspection path.

10. The multi-spot inspection system of claim 9, wherein the first and second detector are the same detector.

11. The multi-spot inspection system of claim 10, wherein a first secondary illumination spot and a second secondary illumination spot are located consecutively in the inspection path, and wherein the illumination power density controller transmits the command signal to the illumination power density attenuator to reduce the illumination power density supplied to at least one of the primary illumination spots when the received signal exceeds a predetermined threshold value at two instances in time separated by a predetermined period of time.

12. The multi-spot inspection system of claim 9, wherein a first secondary illumination spot and a second secondary illumination spot are located consecutively and askew in the inspection path, and wherein the illumination power density controller determines a location of a large particle based on a difference in time between two instances when the received signal exceeds a predetermined threshold value.

13. The multi-spot inspection system of claim 12, wherein the illumination power density controller transmits a command signal to an illumination power density attenuator to reduce the illumination power density at one or more of the primary illumination spots based on the location of the large particle.

14. The multi-spot inspection system of claim 7, wherein the illumination power density controller transmits the command signal to the illumination power density attenuator to reduce the illumination power density supplied to at least one of the primary illumination spots when the signal indicating the second amount of scattered light exceeds a predetermined threshold value.

15. The multi-spot inspection system of claim 7, wherein an amount of radiation directed to the plurality of primary illumination spots is characterized by a first wavelength, and wherein an amount of radiation directed to the at least one secondary illumination spot is characterized by a second wavelength that is different from the first wavelength.

16. The multi-spot inspection system of claim 15, further comprising:
a third detector operable to receive a third amount of light specularly reflected from the at least one secondary illumination spot, wherein a change in wafer height is determined based on a change in location of incidence of the third amount of specularly reflected light received on the surface of the third detector.

17. An apparatus comprising:
a processor; and
a non-transitory, computer-readable medium storing instructions that, when executed by the processor, cause the apparatus to:
receive a first signal indicating an amount of light scattered from at least one secondary illumination spot located ahead of an inspection path of a plurality of primary illumination spots,
determine if the first signal exceeds a predetermined threshold value, and
transmit a command signal to an illumination power density attenuator to reduce an illumination power density of at least one of the plurality of primary illumination spots if the first signal exceeds the predetermined threshold value.

18. The apparatus of claim 17, wherein the instructions further comprise instructions that, when executed by the processor, cause the apparatus to:
receive a second signal indicating a change in location of incidence of an amount of light specularly reflected from the at least one secondary illumination spot on a surface of a detector; and
determine a change in height of the surface of the specimen based on the second signal.

19. The apparatus of claim 17, wherein the first signal indicates an amount of light scattered from a first secondary illumination spot and a second secondary illumination spot consecutively located in the inspection path of the primary illumination spots, and wherein the instructions further comprise instructions that, when executed by the processor, cause the apparatus to:
determine a first time the first signal exceeds a predetermined threshold value;
determine if the first signal exceeds the predetermined threshold value at a second time that is a predetermined period of time after the first time; and
transmit the command signal to the illumination power density attenuator to reduce the illumination power density at one or more of the plurality of primary illumination spots if the first signal exceeds the threshold value at the second time.

20. The apparatus of claim 17, wherein an amount of radiation directed to the plurality of primary illumination spots is characterized by a first wavelength, and wherein an amount of radiation directed to the at least one secondary illumination spot is characterized by a second wavelength that is different from the first wavelength.

\* \* \* \* \*